United States Patent [19]

Angelier et al.

[11] Patent Number: 4,783,973
[45] Date of Patent: Nov. 15, 1988

[54] APPARATUS FOR FREEZING BY MEANS OF A CRYOGENIC LIQUID BIOLOGICAL PRODUCTS PLACED IN STRAWS

[75] Inventors: Nicole Angelier, Echirolles; Joseph Bionda, Voiron; Jean-Yves Thonnelier, Sassenage, all of France

[73] Assignee: L'Air Liquide, Societe Anonyme pour l'Etude et l'Exploitation des Procedes Georges Claude, Paris, France

[21] Appl. No.: 77,671

[22] Filed: Jul. 22, 1987

[30] Foreign Application Priority Data

Jul. 28, 1986 [FR] France ............................. 86 10908

[51] Int. Cl.⁴ .............................................. F25D 3/08
[52] U.S. Cl. ......................................... 62/457; 62/78; 165/61
[58] Field of Search ........................ 62/62, 78, 52, 457; 165/58, 61

[56] References Cited

U.S. PATENT DOCUMENTS

| | | |
|---|---|---|
| 3,024,076 | 3/1962 | Van Wulfften Dalthe ............ 62/62 |
| 3,080,725 | 3/1963 | Cowley et al. ....................... 62/62 |
| 3,151,760 | 10/1964 | Cowley et al. ...................... 62/457 |
| 4,091,632 | 5/1978 | Marchewka et al. ................. 62/1 |
| 4,232,453 | 11/1980 | Edelmann ......................... 62/514 R |
| 4,304,293 | 12/1981 | Scheiwe et al. ........................ 62/62 |
| 4,429,542 | 2/1984 | Sakao et al. ............................ 62/78 |
| 4,455,842 | 6/1984 | Granlund ............................... 62/78 |
| 4,537,034 | 8/1985 | Crouch ................................. 62/78 |

FOREIGN PATENT DOCUMENTS

| | | |
|---|---|---|
| 0090599 | 10/1983 | European Pat. Off. . |
| 0150146 | 7/1985 | European Pat. Off. . |
| 0181235 | 5/1986 | European Pat. Off. . |
| 0184417 | 6/1986 | European Pat. Off. . |
| 1401608 | 10/1968 | Fed. Rep. of Germany . |
| 3125345 | 1/1983 | Fed. Rep. of Germany . |
| 3225672 | 1/1984 | Fed. Rep. of Germany . |
| 1296171 | 5/1962 | France . |
| 1566664 | 5/1969 | France . |
| 2468908 | 5/1981 | France . |

*Primary Examiner*—Ronald C. Capossela
*Attorney, Agent, or Firm*—Young & Thompson

[57] ABSTRACT

A thermally insulated enclosure (1) containing a bath (20) of liquid nitrogen. The enclosure contains a case (3) of flat shape provided with a thermal insulation (4) whose performance is lower than that (2) of the enclosure (1) and comprising, on one hand, supports (17) for supporting straws in a horizontal plane, and, on the other hand, a heater (8) for heating the lower wall (7) and/or the cover (6) of the case. Application in the freezing of animal or human embryos.

11 Claims, 2 Drawing Sheets

APPARATUS FOR FREEZING BY MEANS OF A CRYOGENIC LIQUID BIOLOGICAL PRODUCTS PLACED IN STRAWS

The present invention relates to an apparatus for freezing biological products placed in small straws, of the type comprising a thermally insulated enclosure adapted to contain a bath of cryogenic liquid.

The freezing of animal or human embryos, placed in straws in a cryoprotective liquid, requires the following of a very precise temperature program adapted to the embryo and its container; it is the result of experience and must be scrupulously followed to ensure the survival of the embryo.

By way of example, a temperature program comprises the following principal stages:

a first reduction of temperature from ambient temperature to a supercooling level of the cryoprotective liquid ($-5°$ to $-7°$ C.) at a rate of a few ° C./min;

at this temperature, a "seeding" is effected, i.e crystallization is brought about by a brief and intense freezing, for example by bringing a previously-cooled metallic mass into contact with the straws; the temperature then rises to the temperature of crystallization of the medium;

thenceforth, the reduction of the temperature is resumed at the rate of on the order of 0.2° to 0.5° C./min to around $-35°$ C., at which temperature the straws may be immersed in liquid nitrogen and then stored in a cryobiological container.

If, as is usually the case, a plurality of straws are frozen at the same time, a strict thermal homogeneity between all the straws must be conformed to so as to be able to effect the (automatic or manual) seeding on all the straws at the same time and also to use only a single temperature sensing device placed for example in a reference straw for controlling the temperature programmer.

Many types of biological freezers exist which employ as a freezing source liquid nitrogen or mechanical cold of the alcohol bath type. Some apparatus employing liquid nitrogen are particularly well adapted, since they enable the freezing and the final immersion in the liquid nitrogen to be effected in turn in the same enclosure.

However, liquid nitrogen is a powerful freezing source which must be used with precaution if it is desired to follow the defined program precisely on a large number of straws at the same time.

Known solutions employ liquid nitrogen in the following way:

In a first type of apparatus, the straws are disposed in an insulated enclosure in which a fan ensures the thermal homogeneity of the gas. Liquid nitrogen is injected into the enclosure under the control of a regulator and the fan ensures the dispersion of the liquid. The freezer is connected to a liquid nitrogen container which must be equipped with a pressurization device, and an electrically-operated valve controlled by the regulator regulates the introduction of nitrogen into the enclosure.

This type of equipment is well adapted to present needs of specialized laboratories, but the development of the technique of embryo freezing requires apparatus which, owing to their low price, their simplicity and their sturdy construction, better satisfy the particular conditions of utilization: freezing on the site (on the farm), transportable equipment, utilization by unspecialized personnel.

Further, freezers are also known in which the cooling is ensured by the simple use of the thermal gradient in vapours above a bath of liquid nitrogen: the straws are progressively lowered into the vapours until they are immersed in the liquid. These apparatus are simple, but do not permit the obtainment of very small and perfectly-controlled cooling slopes, which renders them unsuitable in the freezing of embryos.

An object of the invention is to provide a transportable and autonomous apparatus which is particularly simple and sturdy in construction and enables even unspecialized personnel to carry out the freezing of embryos in a reliable manner.

The invention therefore provides an apparatus of the aforementioned type, wherein the enclosure contains a case of flat shape provided with a thermal insulation whose performance is lower than that of the enclosure and comprising, on one hand, means for supporting the straws in a horizontal plane, and, on the other hand, means for heating the lower wall and/or the cover of the case.

In an advantageous embodiment, said support means are thermally insulating and adapted to carry all the straws in a single horizontal plane. In this case, the straws may be disposed between two horizontal metallic plates immediately adjacent to the straws provided inside the case.

An embodiment of the invention will now be described with reference to the accompanying drawings, in which.

Figure 1:
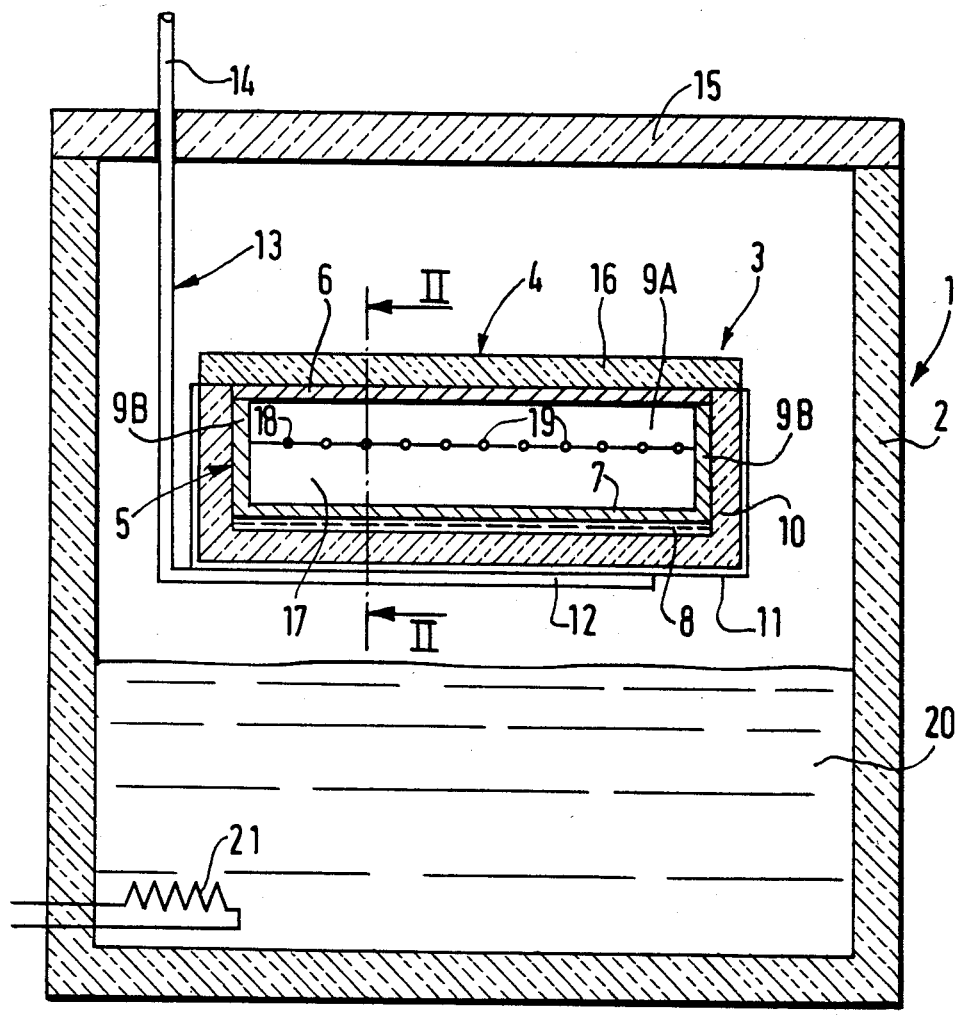
FIG. 1 is a vertical sectional view of a freezing apparatus according to the invention.

The embryo freezing apparatus shown in FIG. 1 comprises an outer enclosure 1 provided with a thermal insulation 2 of a high performance, and a case 3 provided with a thermal insulation 4 of a distinctly lower performance.

The case 3 has a flat parallel-sided shape and essentially comprises a vessel 5 and a removable cover 6 both of thick metal, for example having a thickness on the order of several millimeters, this thickness being the same for all the sides of the vessel and cover for reasons of convenience of manufacture.

The vessel 5 has a horizontal bottom 7, to the lower side of which is adhered an electric resistor film 8, and lateral walls 9A, 9B. It is fitted into a dish 10 of insulating material, for example a rigid foam of plastics material, which is itself fitted into a dish 11 of sheet metal. The latter is secured to the lower horizontal branch 12 of two L-shaped supports 13, the vertical branch 14 of these supports slidably extending through two orifices provided in the removable cover 15 of the enclosure 1.

Means (not shown) enable the supports 13 to be positioned at several heights to allow the case 3 to be put in at least three different positions in the enclosure 1, namely an upper position close to the upper edge of the lateral walls of the enclosure, an intermediate position shown in FIG. 1, and a lower position close to the lower end wall of the enclosure.

Further, the insulation 4 of the case is completed by a plate 16 of insulating material secured to the outer side of the cover 6.

Provided in a position parallel to the two lateral sides 9A of the case and within the latter, are two horizontal straw carriers 17. Each straw carrier is formed by a strip of insulating material, for example plastics material, placed on the bottom 7 and fixed by its ends to the other two lateral sides 9B of the case. These strips are provided in their upper side with a series of transverse semi-circular recesses 18 which are in coaxial alignment in pairs. Thus, a series of straws 19, formed by long tubes of plastics material of small diameter, may be disposed parallel to one another in a single horizontal layer, each of the straws being carried by a recess 18 of a straw carrier 17 and by the associated recess of the other straw carrier. The height of the case is only slightly greater than that of the straw carriers provided with the straws 19.

In operation, the enclosure 1 is partly filled with liquid nitrogen to constitute a bath 20 of this substance up to a predetermined height; an embryo to be frozen is disposed in each straw at a given distance from its ends, the straws are loaded in the case and the thus-loaded case 3 provided with its cover is placed in its intermediate position where it is fully immersed in the cold nitrogen vapors above the bath 20. The straws are then in the same horizontal plane and all the embryos are substantially aligned along the same horizontal line.

A constant evaporation of the nitrogen, for example on the order of 1 1/hr, achieved either by natural entries of heat or by means of an electric resistor 21 provided close to the bottom of the enclosure 1, creates around the case a constant supply of cold serving to freeze the straws.

The insulation 4 of the case is so chosen that the rate of the reduction of temperature within the case produced by this supply of cold is slightly higher than the highest rate required in the considered freezing program, namely a few ° C/min.

In order to adjust the rate of the reduction of temperature to a prescribed value, a flow of heat by the Joule effect is further supplied to the case controlled in a precise manner by means of the resistor 8 through wires (not shown) extending in the supports 13 to a source of electric current (not shown) outside the enclosure 1. This supply of heat is homogenized or diffused throughout the area of the bottom 7 of the case by the great thickness of this bottom and is controlled by a regulator (not shown) by means of temperature data provided by a thermocouple (not shown) with which one of the straws is provided.

Thus, the straws are confined in a restricted space which is almost isothermic but in which there nonetheless occurs a certain upward natural convection, and the straws are subjected, from the thermal point of view, only to this single natural convection.

Owing to the manner in which the supply of cold and heat are ensured, the isothermic surfaces are practically horizontal throughout the case and in particular, in view of the disposition of the straws in a single horizontal layer, all the straws are at each instant at a uniform temperature. This makes it possible to follow precisely the prescribed temperature program for all the straws simultaneously, the temperature of the straws being regulated at each instant by the regulation of the power dissipated in the resistor 8 from data corresponding to a single one of the straws.

When a chosen supercooling temperature (for example, $-7°$ C.) is reached, the case is raised to its upper position and the cover 15 of the enclosure is opened.

The case is then in an environment formed by a mixture of cold nitrogen and ambient air at a temperature of around said supercooling temperature. The cover 6 of the case is then opened and the seeding is effected by bringing into contact with all the straws at the position of the embryos a horizontal metal bar, termed "thermal inductor", previously-cooled in the liquid nitrogen.

Thereafter, the case and then the enclosure 1 are closed and the case is lowered to its intermediate position and the temperature lowering program is carried out as before down to a given freezing temperature (for example $-35°$ C.).

Lastly, the case is lowered to its lower position to immerse it in the bath 2 of liquid nitrogen and effect the final embryo-freezing stage, before their transfer to a cryobiological storage container.

The device just described is economical, sturdy and reliable owing to the complete absence of moving parts, such as a motor, fan, electrically-operated valves or stirring means.

Figure 2:
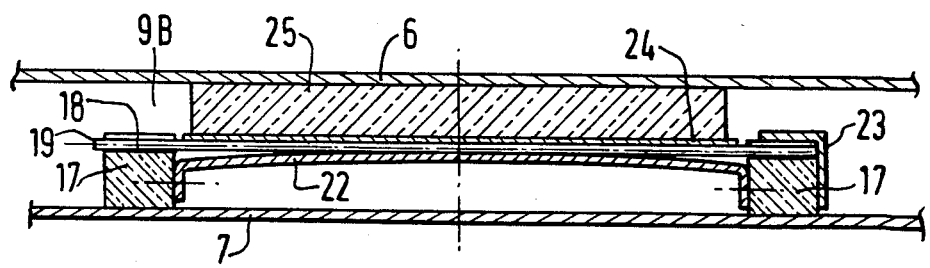
FIG. 2 is a partial sectional view, to an enlarged scale, of a variant, taken on a line corresponding to line II—II of FIG. 1.

FIG. 2 illustrates a variant for still further improving the homogeneity of the reductions of temperature of the various straws by positively ensuring the presence of a horizontal isotherm at their level, at least at the position of the embryos. For this purpose, there are disposed horizontally, just above and just below the layer of straws, two thin metallic plates having a thickness of 5/20 to 1 mm, which are not in thermal contact with the case 3. In the embodiment of FIG. 2, the lower plate 22, which has a slightly curved, convex or crowned upper side, is fixed by two opposed sides to the two straw carriers 17, one of which carries an L-section member 23 serving to longitudinally position one end of the straws.

Midway between the straw carriers, which corresponds to the position of the embryos, this plate 22 is at the level of the lower generatrix of the recesses 18 and therefore of the straws 19.

The upper plate 24 has a dimension, in the longitudinal direction of the straws, which is slightly less than the distance between the two straw carriers. It is planar, horizontal and secured to the lower side of a parallel-sided plate of flexible foam material 25 which is fixed to the lower side of the cover 6 of the case and is thermally insulating.

When the case is loaded with straws, the region of the latter containing the embryos comes into contact with the lower plate 22 then, when the cover 6 is closed, the upper plate 24 comes to bear slightly, with a force limited by the elasticity of the foam plate 25, against the straws. During the drop in temperature, the plates 22 and 24, being thermally conductive, each define an isothermic surface which ensures a very high homogeneity of the temperature of the embryos. This would moreover remain true if the plates were not in contact with the straws but, owing to this contact, these plates afford, by their thermal inertia, an improved regulation of the second temperature drop after the seeding.

Figure 3:
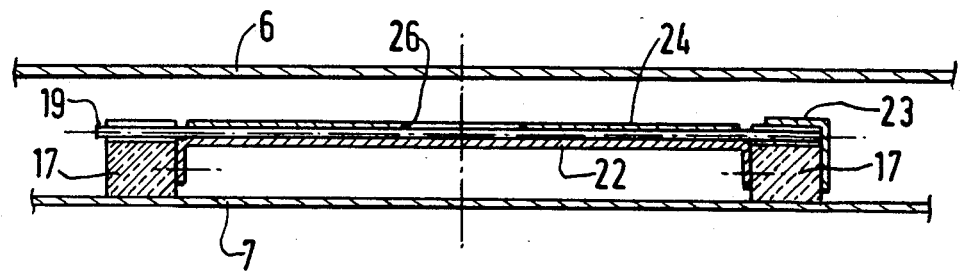
FIG. 3 is a view similar to FIG. 2 of another variant.
Figure 4:
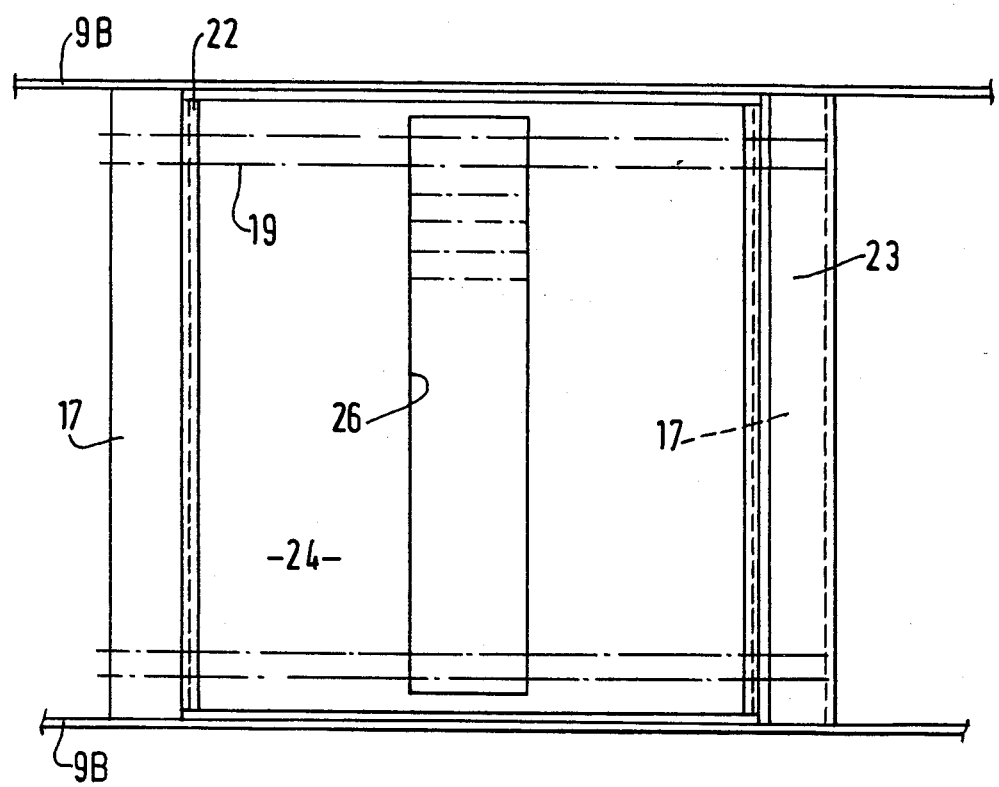
FIG. 4 is a top plan view of the apparatus of FIG. 3.

In the variants shown in FIGS. 3 and 4, the plate 22 is planar and the plate 24 is merely placed on the straws. Further, the plate 24 has a transverse opening 26 which exposes all the straws in the region of the position of the embryos so that the seeding can be carried out without withdrawing this plate.

In another variant, the upper side of the cover 6 of the case may also be provided with heating means, such as an adhered resistor film, the heat being then supplied to the two large sides of the case. This second resistor is particularly desirable in a variant of the apparatus (not shown) in which the cover 6 is devoid of any thermal insulation.

What is claimed is:

1. An apparatus for freezing biological products placed in straws, the apparatus comprising an enclosure having a first thermal insulation for containing a bath of cryogenic liquid, a case of flat shape including a lower wall and a cover and located in the enclosure and provided with a second thermal insulation, the thermal insulating power of said first insulation being substantially greater than that of said second insulation, the case comprising means for supporting straws in a horizontal plane and means for heating at least one of elements consisting of the lower wall and the cover of the case.

2. An apparatus according to claim 1, wherein said support means are thermally insulating and adapted to carry all the straws in a single horizontal plane.

3. An apparatus according to claim 2, comprising two horizontal metallic plates inside the case, between which plates the straws are disposed 4. An apparatus according to claim 3, wherein at least one of the plates is in contact with the straws.

5. An apparatus according to claim 3, wherein an upper plate of said plates defines a window perpendicular to the longitudinal direction of the straws.

6. An apparatus according to claim 3, wherein a lower plate of said plates is integral with the case, and an elastically yieldable thermally insulating support is interposed between and connected to the upper plate and the cover of the of the case for carrying the upper plate.

7. An apparatus according to claim 1, comprising a support for the case and permitting the positioning of the case at different heights in the enclosure.

8. An apparatus according to claim 1, wherein at least one wall of the case provided with heating means comprises means for diffusing heat in the plane thereof.

9. An apparatus according to claim 8, wherein the case comprises very thick metal walls.

10. An apparatus according to claim 1, wherein the cover of the case is devoid of heat insulation and is provided with heating means.

11. An apparatus according to claim 1, wherein said heating means comprise a planar electrical resistor adhered to an outer side of the associated wall.

* * * * *